United States Patent [19]
Lautenschläger

[11] Patent Number: 4,734,260
[45] Date of Patent: Mar. 29, 1988

[54] CUVETTE

[75] Inventor: Werner Lautenschläger, Leutkirch, Fed. Rep. of Germany

[73] Assignee: AGW Analysen-Geräte GmbH, Leutkirch, Fed. Rep. of Germany

[21] Appl. No.: 845,590

[22] Filed: Mar. 28, 1986

[30] Foreign Application Priority Data

Mar. 30, 1985 [DE] Fed. Rep. of Germany ... 8509640[U]

[51] Int. Cl.$^4$ ............................................. G01N 21/03
[52] U.S. Cl. ..................................... 422/58; 422/102; 422/246; 436/165; 356/246; 73/864.91
[58] Field of Search .................. 422/58, 102; 356/246; 436/165; 73/864.91

[56] References Cited

U.S. PATENT DOCUMENTS

| | | | |
|---|---|---|---|
| 3,552,865 | 1/1971 | Leung et al. | 356/246 |
| 4,088,448 | 5/1978 | Lilja et al. | 422/102 |
| 4,203,840 | 5/1980 | Stoepper et al. | 422/101 |
| 4,244,916 | 1/1981 | Guigan | 422/72 |
| 4,391,780 | 7/1983 | Boris | 422/102 |
| 4,615,360 | 10/1986 | Jacobs | 422/64 |

OTHER PUBLICATIONS

Fisher Scientific Catalogue, Allied Company 1983, pp. 1128-1129.

Primary Examiner—Kenneth M. Schor
Assistant Examiner—Lori-Ann Cody
Attorney, Agent, or Firm—Spencer & Frank

[57] ABSTRACT

A cuvette for liquid samples, particularly for absorption spectrum analysis. The curvette has a multi-part housing structure enclosing a thin sample chamber which is delimited by two radiation transmitting discs and is provided with two bores leading to the sample chamber. Stoppers of a plastic material are inserted into the respective bores, each stopper being provided with a thin longitudinal channel which can be sealed by means of a hollow needle whose tip is inserted into it or by means of a closing needle.

5 Claims, 3 Drawing Figures

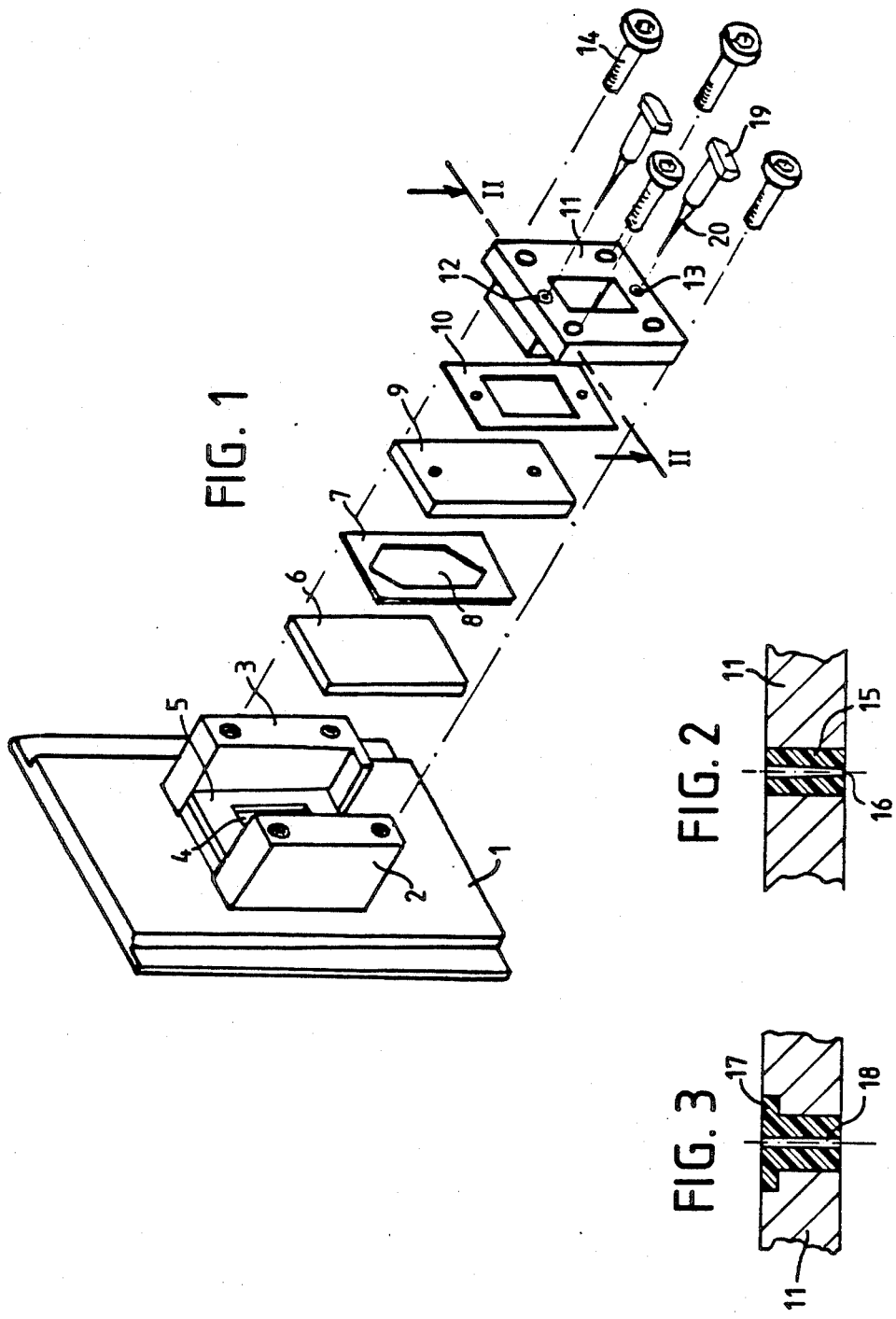

CUVETTE

BACKGROUND OF THE INVENTION

The invention relates to a cuvette for liquid or gaseous samples, particularly for absorption spectrum analysis, the cuvette comprising a multi-part housing structure which encloses a thin sample chamber that is delimited by two radiation transmitting discs and is provided with two bores leading to the sample chamber.

The bores serve as fill and ventilation channel for the sample chamber and, in prior art cuvettes of this type, are provided with a screwed-in connecting nipple which itself is provided with a precisely ground, hollow, conical connecting piece or a screw connection as is well known for the tight connection of injection needles with multi-use injection syringes. To fill the cuvette, the syringe containing the sample fluid is connected with the fill end and, if fluid escapes at the other end after filling of the sample chamber, the latter is closed by means of a stopper. Then the syringe is removed and the fill end is likewise closed.

The drawbacks here are that, compared to the small capacity of the sample chamber, a relatively large volume of sample fluid is required to fill the connecting nipples and that sample fluid is usually pressed out when the ends or nipples are sealed, which is annoying and makes work more difficult. On the other hand, air inclusions often remain in the channels.

SUMMARY OF THE INVENTION

It is the object of the invention to provide a cuvette which is simpler, can be filled and sealed cleanly without the inclusion of air and which requires less sample fluid.

This is accomplished by the invention, starting with a cuvette of the above-mentioned type, in that plastic stoppers are inserted into the bores, each stopper being provided with a thin longitudinal channel which can be closed by means of the tip of a hollow needle or a closing needle. As a practical matter, the longitudinal channel is conically tapered toward the interior. Preferably, the stopper is composed of polytetrafluoroethylene, a common sealing material which is resistant to most sample fluids. The stopper may have a simple cylindrical shape and may be provided with sealing collars at its outer end, if required. Moreover, for easier insertion, the stopper may be given a flange-like extension. Preferably it is flush with the surface of the housing.

The hollow needle for filling or extracting the sample chamber may be an injection needle which means that advantageously the needle need not be removed from the syringe for this process phase. In particular, however, the conventional throw-away tip of a pipette may also be used as the hollow needle and may be connected tightly with the sample chamber simply by inserting it. Needles having a solid cross section which, for easier manipulation, may be provided with a handle member, serve to seal the opening. Any air possibly still contained in the fill channel is thus expelled toward the exterior.

Since the bore in the housing need not have an internal thread, such cuvette closures can be manufactured extremely simply and inexpensively. Due to the fact that the cross section of the fill and ventilation channel as a whole is thin, not much sample fluid beyond the capacity of the sample chamber is required.

BRIEF DESCRIPTION OF THE DRAWINGS

One embodiment of the invention will be described below with reference to the drawing, in which:

FIG. 1 is a exploded view of a cuvette.

FIG. 2 is a sectional view of a closing stopper, drawn to a larger scale and taken along line II—II.

FIG. 3 is another embodiment of the closing stopper in a corresponding view.

DESCRIPTION OF THE PREFERRED EMBODIMENTS

According to FIG. 1, the housing structure of the cuvette is composed of a base plate 1 as well as a linear and an angular mounting block 2 and 3. The base plate is provided with a rectangular window 4. Between mounting blocks 2 and 3, there is inserted an elastic insert 5 which is likewise provided with a window. This is followed by an infrared transmitting window pane 6 of a salt crystal, a spacer member 7 less than 0.1 mm thick and provided with a cut-out which forms the sample chamber, a further window pane 9 provided with two bores, a sealing disc 10 provided with a window and two bores, and finally a metal pressure member 11, likewise provided with a window. All of the components 6 to 11 have the same outlines. Pressure member 11 is provided with two bores 12 and 13 which are flush with the bores of seal 10 and window pane 9 and thus are in communication with sample chamber 8. All parts are held together by means of hollow screws 14.

FIG. 2 shows pressure member 11 and bore 12 in a sectional view. A stopper 15 of polytetrafluoroethylene is inserted into the bore and is provided with a central longitudinal channel 16 which is conically tapered toward sample chamber 8.

In the embodiment according to FIG. 3, the stopper has a collar 17 and a non-tapered central longitudinal channel 18.

Either the injection needle of a syringe or the tip of a pipette or a closing needle can be tightly inserted into the longitudinal channels. Examples of closing needles are shown in FIG. 1. They are composed of a handle member 19, which may be made of plastic, and a needle tip 20.

I claim:

1. Cuvette for storing a liquid sample, comprising: a housing having an exterior surface and enclosing a thin sample chamber; two radiation transmitting discs disposed within said housing and delimiting mutually opposed sides of said chamber, one of said discs and said housing each being provided with two bores, said bores of said housing and said bores of said one disc being aligned and extending between the exterior surface of said housing and said chamber to provide communication between the exterior and said chamber; and two stoppers of plastic material each inserted into a respective one of said housing bores and each of said two stoppers being provided with a narrow longitudinal channel communicating with said chamber through its respective bore and closeable by a needle.

2. Cuvette according to claim 1, wherein each of said longitudinal channels of said stoppers is conically tapered toward said chamber.

3. Cuvette according to claim 1, wherein each of stoppers is made of polytetrafluoroethylene.

4. Cuvette as defined in claim 1 further comprising a closing needle insertable into said channel in one of said two stoppers for sealing said channel.

5. Cuvette as defined in claim 1 for holding a sample to be subjected to absorption spectrum analysis, wherein at least one of said discs is made of a salt crystal and transmits infrared radiation.

* * * * *